(12) United States Patent  
Bensoussan

(10) Patent No.: US 7,752,691 B2  
(45) Date of Patent: Jul. 13, 2010

(54) SIDS-PREVENTATIVE MATTRESS

(76) Inventor: Jose Bensoussan, 9955 Durant Dr., Suite #203, Beverly Hills, CA (US) 90212

( * ) Notice: Subject to any disclaimer, the term of this patent is extended or adjusted under 35 U.S.C. 154(b) by 0 days.

(21) Appl. No.: 12/079,692

(22) Filed: Mar. 28, 2008

(65) Prior Publication Data

US 2009/0241264 A1     Oct. 1, 2009

(51) Int. Cl.  
*A47C 16/00* (2006.01)

(52) U.S. Cl. ............................. 5/655; 5/120

(58) Field of Classification Search ........... 5/655, 5/731, 732, 735, 631, 931, 603, 604, 606, 5/638, 652.1, 655.9, 724–726, 120, 122; 297/452.56  
See application file for complete search history.

(56) References Cited

U.S. PATENT DOCUMENTS

| | | | | |
|---|---|---|---|---|
| 2,924,832 | A * | 2/1960 | Knowles | 5/606 |
| 3,315,282 | A * | 4/1967 | Lowery et al. | 5/638 |
| 4,639,960 | A * | 2/1987 | Quillen et al. | 5/710 |
| 4,989,284 | A * | 2/1991 | Gamm | 5/653 |
| 5,214,087 | A | 5/1993 | Braden et al. | |
| 5,288,135 | A * | 2/1994 | Forcier et al. | 297/452.21 |
| 5,561,876 | A | 10/1996 | Petruzella | |
| 5,561,879 | A | 10/1996 | Everall | |
| 5,687,436 | A * | 11/1997 | Denton | 5/653 |
| 5,697,113 | A * | 12/1997 | Shatz et al. | 5/655 |
| 6,263,526 | B1 * | 7/2001 | Tu | 5/109 |
| 6,425,152 | B1 | 7/2002 | Quarles | |
| 6,460,207 | B1 | 10/2002 | Papay et al. | |
| 7,076,822 | B2 * | 7/2006 | Pearce | 5/655.5 |
| 7,234,181 | B1 | 6/2007 | Griggs | |
| 2006/0162088 | A1 | 7/2006 | Daly | |
| 2006/0179568 | A1 | 8/2006 | Campbell | |
| 2006/0218726 | A1 | 10/2006 | Waters et al. | |
| 2007/0283502 | A1 | 12/2007 | Tullous | |

OTHER PUBLICATIONS

International Searching Authority of WIPO, International Search Report for PCT/US09/37222, May 26, 2009.

* cited by examiner

*Primary Examiner*—Peter M Cuomo  
*Assistant Examiner*—Nicholas Polito

(57) ABSTRACT

An infant mattress includes a core and a cover. The core is made from a resilient material and has a top surface and a bottom surface. The top surface is inclined with respect to the bottom surface and includes a depression. The cover covers the core and includes a mesh-like material that forms an inclined hammock over the depression. The head and torso of an infant are placed on the hammock. One or more sidewalls of the depression may have one or more openings to facilitate air circulation within the depression cavity. The external ends of the openings may connect to an air or aerosol source to inject air or aerosols into the depression cavity. The core may be coated with an impermeable water-proofing layer.

15 Claims, 10 Drawing Sheets

SIDS-PREVENTATIVE MATTRESS

FIELD OF THE INVENTION

The present invention relates generally to infant mattresses. More particularly, various embodiments disclose an infant mattress that is designed to prevent Sudden Infant Death Syndrome (SIDS) and to help reduce the risk of plagiocephaly.

BACKGROUND OF THE INVENTION

Sudden Infant Death Syndrome (SIDS) is a significant cause of death among infants in their first year of life. To date, the underlying causes remain unexplained. The most recent research has shown, however, a connection between SIDS and blockage of the upper respiratory system. Consequently, many medical authorities today recommend that infants be placed on their backs with the spines straight (the so-called straight head position, or SHP). SHP ensures that the upper respiratory system is maximally opened. The lay back position reduce the possibility of re-breathing exhaled air. Physicians further recommend that infants be positioned such that their torsos are slightly elevated to reduce the risk of gastroesophageal reflux.

Because SIDS presents such a serious threat to infants, there is an immediate need for infant mattresses that assist in the positioning of an infant so as to conform with current best practices for reducing SIDS. Additionally, it has been noted that some infants develop a flat area on the skull (known as positional plagiocephaly) during their first few months from sleeping on their backs all the time on a flat surface. It is therefore desirable to provide a mattress that will avoid infant plagiocephaly.

SUMMARY

Various embodiments disclose an infant mattress that includes a core mattress having top and bottom surfaces and a mattress cover. The top surface has a first depression sized to at least partially accept the torso and head of an infant. The mattress cover includes a mesh material to cover at least a portion of the depression. The mesh material forms a hammock over the bottom surface of the depression, and at least the torso and head of the infant may be disposed on this hammock.

In preferred embodiments the mattress cover forms a bag-like structure into which the core mattress is disposed. In such embodiments the mattress cover may further comprise a closing mechanism to close an opening of the bag-like structure.

In various embodiments at least one sidewall of the first depression comprises an opening for providing air or aerosols to the depression. An external end of the opening may be adapted to connect to a supply tube that supplies air, oxygen, aerosols or combinations thereof to the cavity formed by the first depression.

In various preferred embodiments the top surface is inclined with respect to the bottom surface. An anterior end of the first depression includes a stopping surface that abuts against the buttocks or upper legs of the infant to prevent the infant from sliding towards the anterior end of the infant mattress.

In some embodiments the infant mattress further includes a stiffening system to impart rigidity to the core mattress. The stiffening system may be disposed within the core mattress.

In yet other embodiments the bottom surface of the first depression further comprises a tray, an absorbent material, or both for collecting fluids from the infant. In specific embodiments the tray, absorbent material or both are disposed within a second depression within the first depression. In certain embodiments the secretion tray serves as the stiffening system for the core mattress.

DETAILED DESCRIPTION

Figure 1:
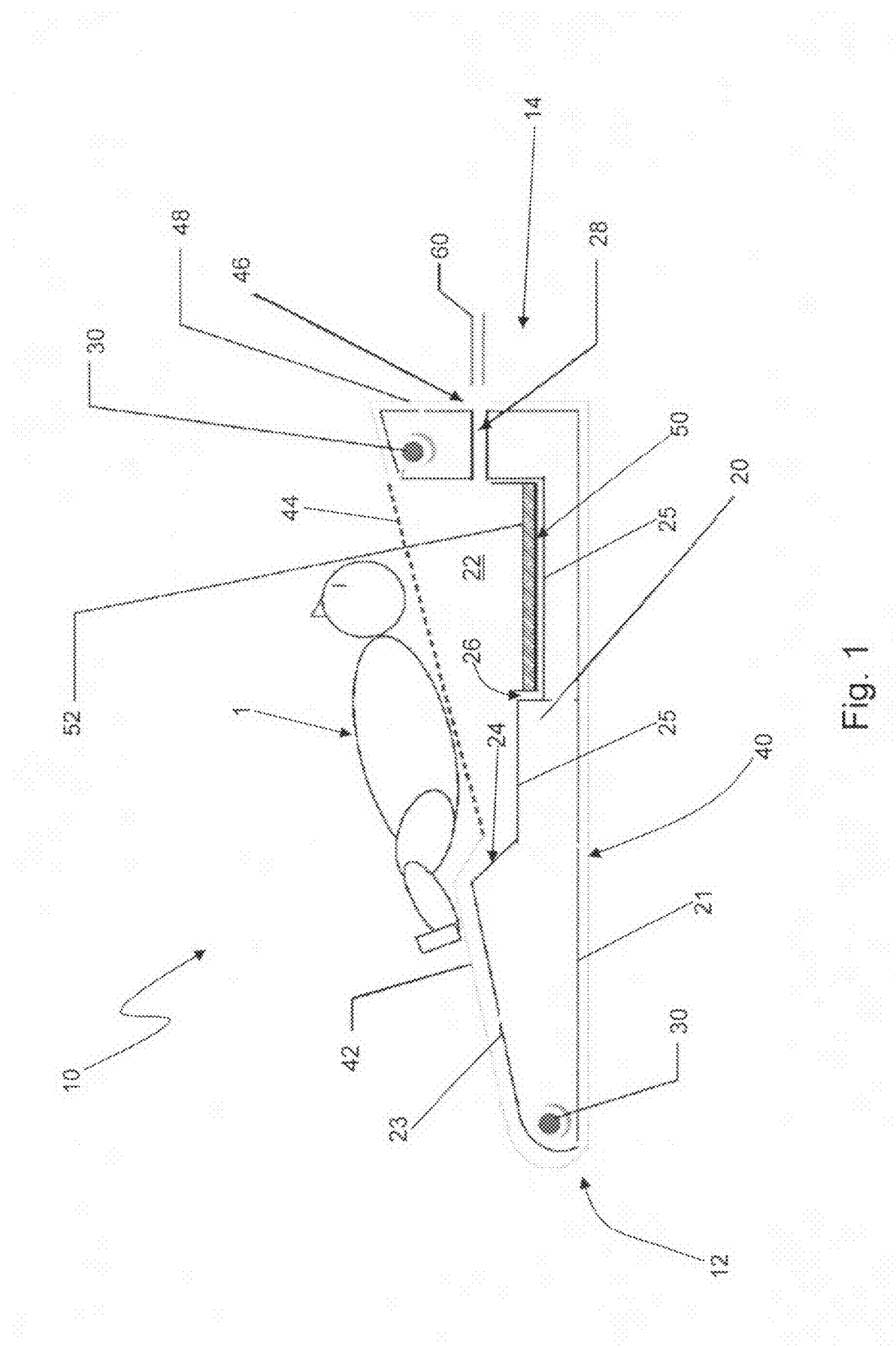
FIG. 1 is cross-sectional view of an embodiment mattress along a centerline of the mattress from anterior to posterior ends.
Figure 2:
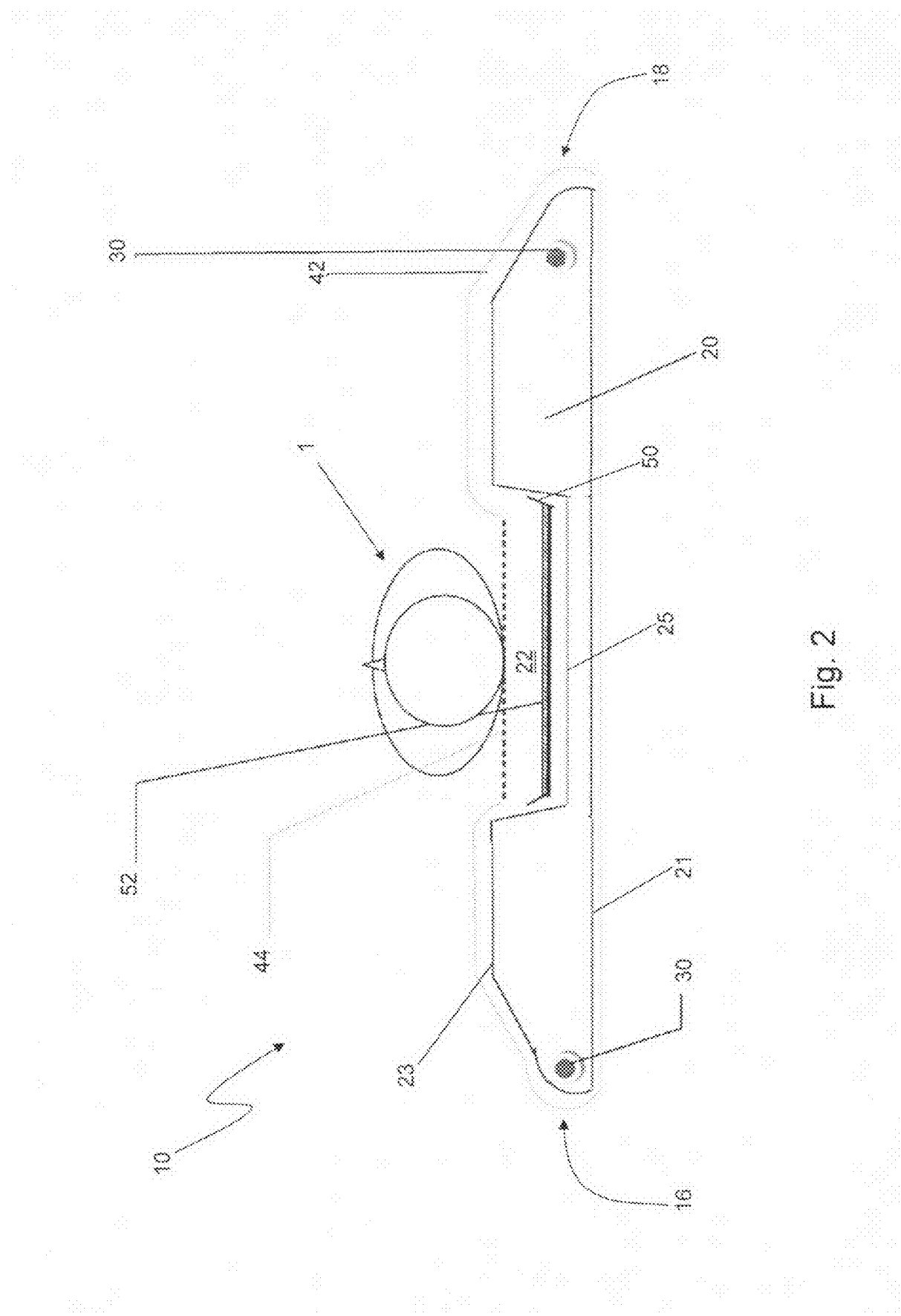
FIG. 2 is a cross-sectional view of an embodiment mattress along a centerline of the mattress from left to right sides.
Figure 3:
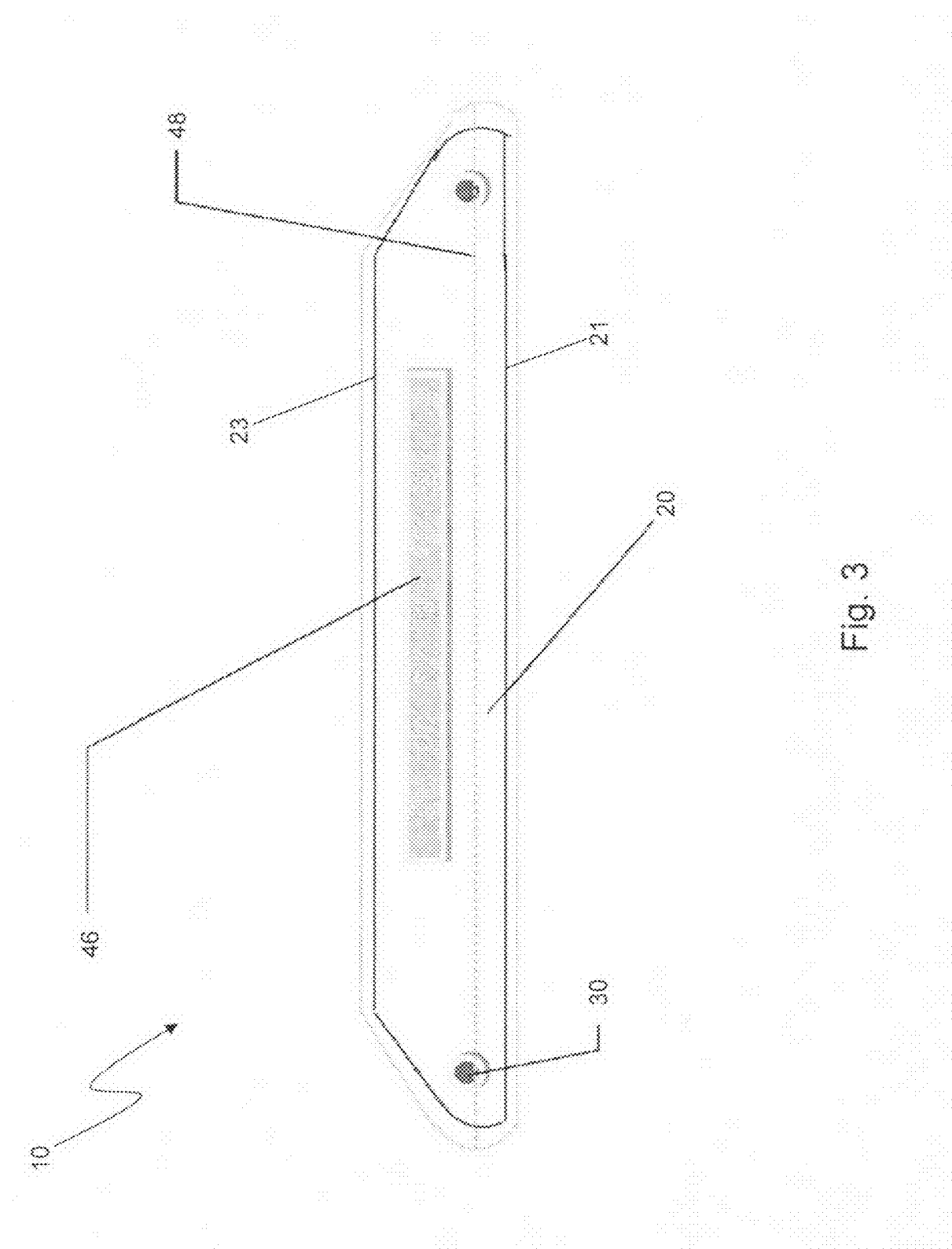
FIG. 3 is a side view of the posterior end of an embodiment mattress with a mattress sheet.
Figure 4:
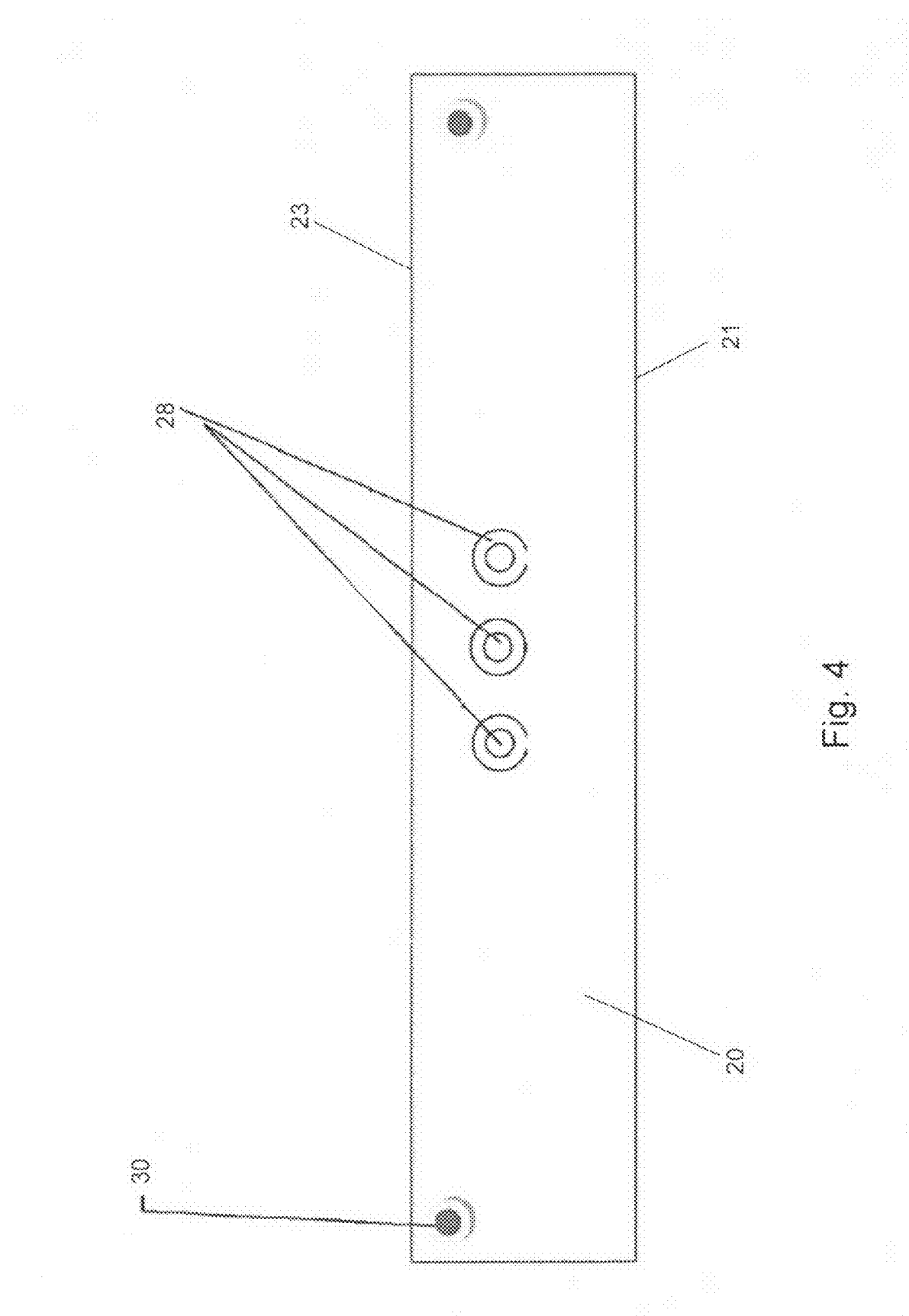
FIG. 4 is a side view of the posterior end of an embodiment mattress without the mattress sheet.
Figure 5:
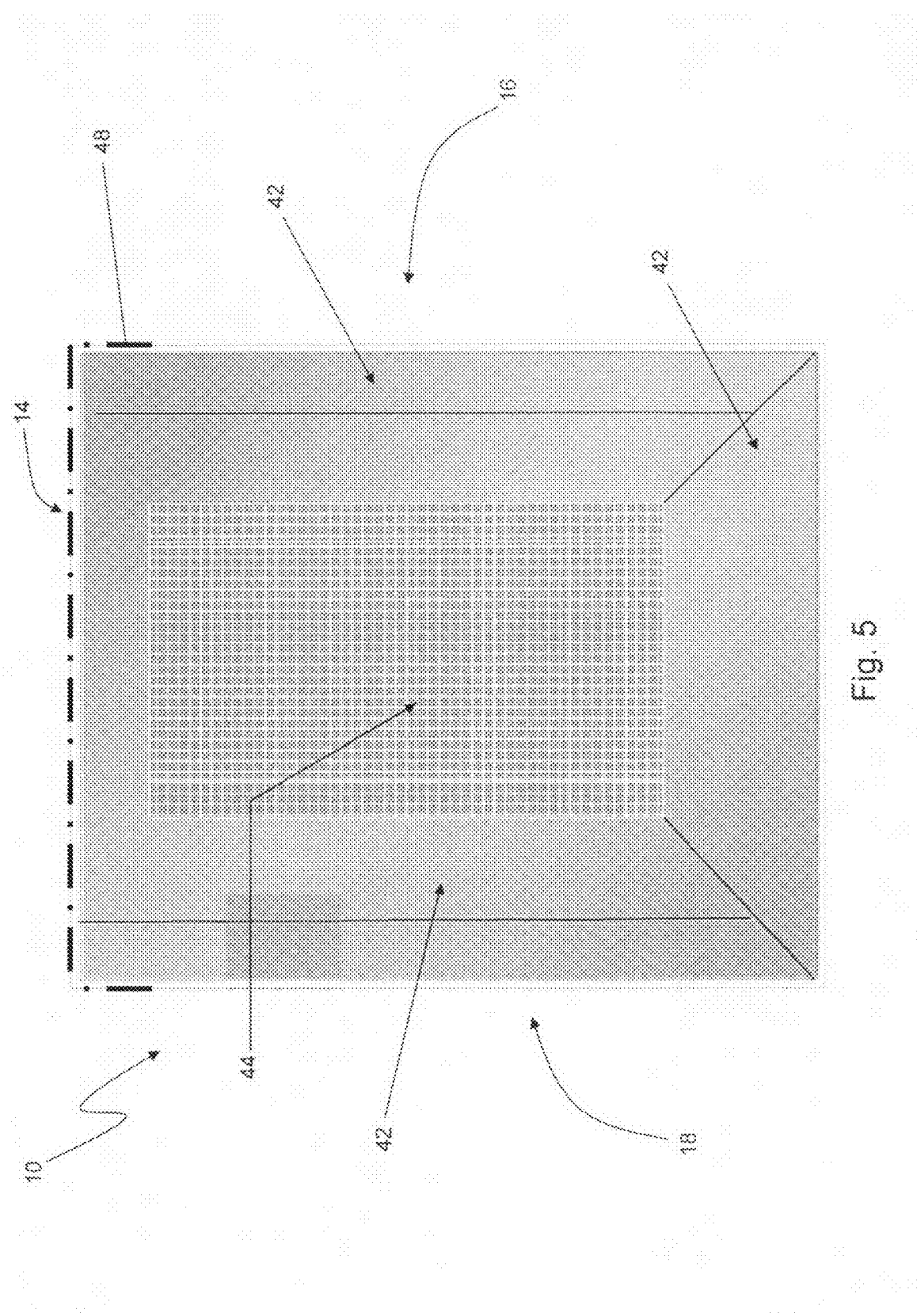
FIG. 5 is a top view of an embodiment mattress with a mattress sheet.
Figure 6:
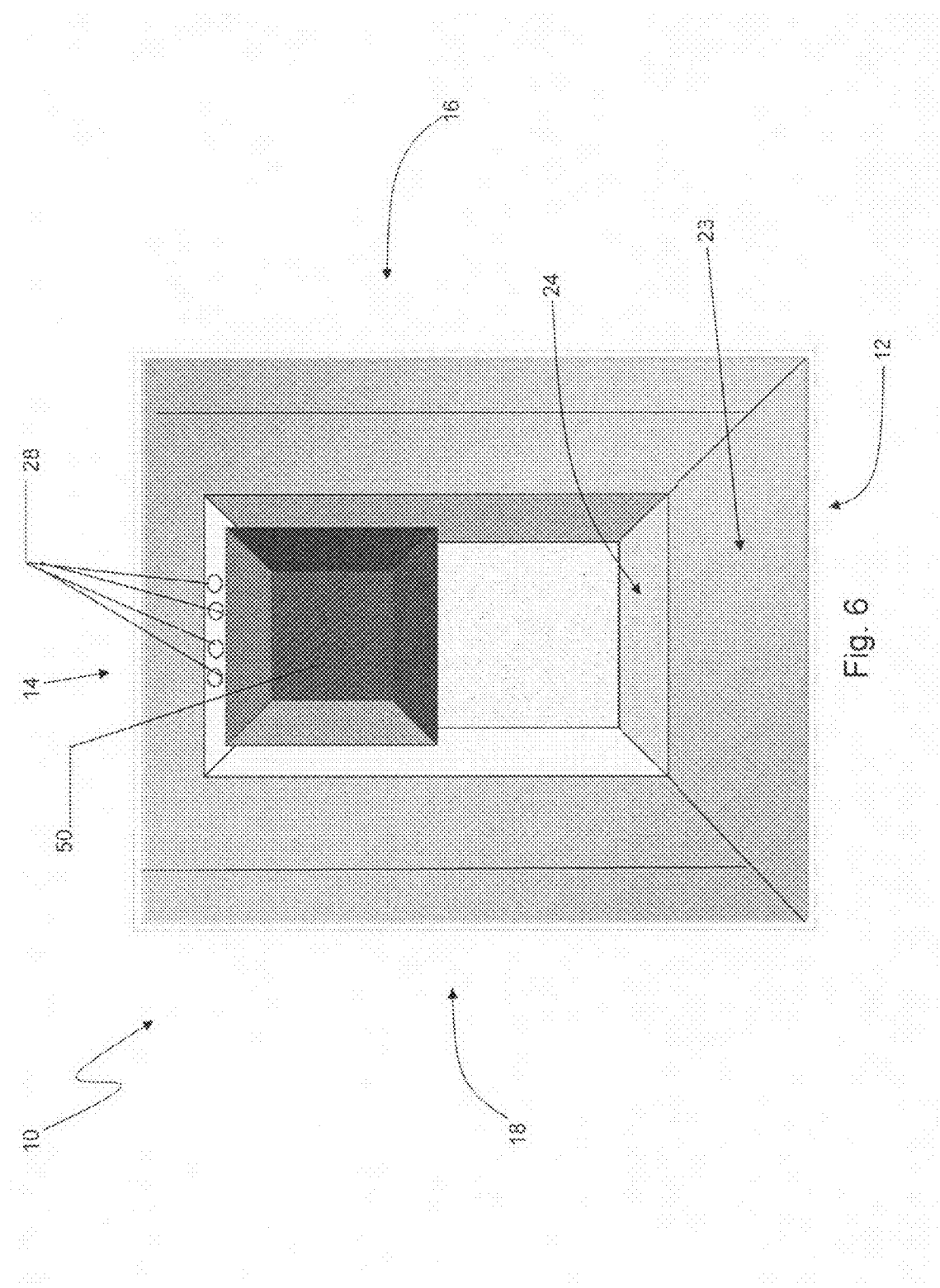
FIG. 6 is a top view of the embodiment mattress of FIG. 4 without the mattress sheet.
Figure 7:
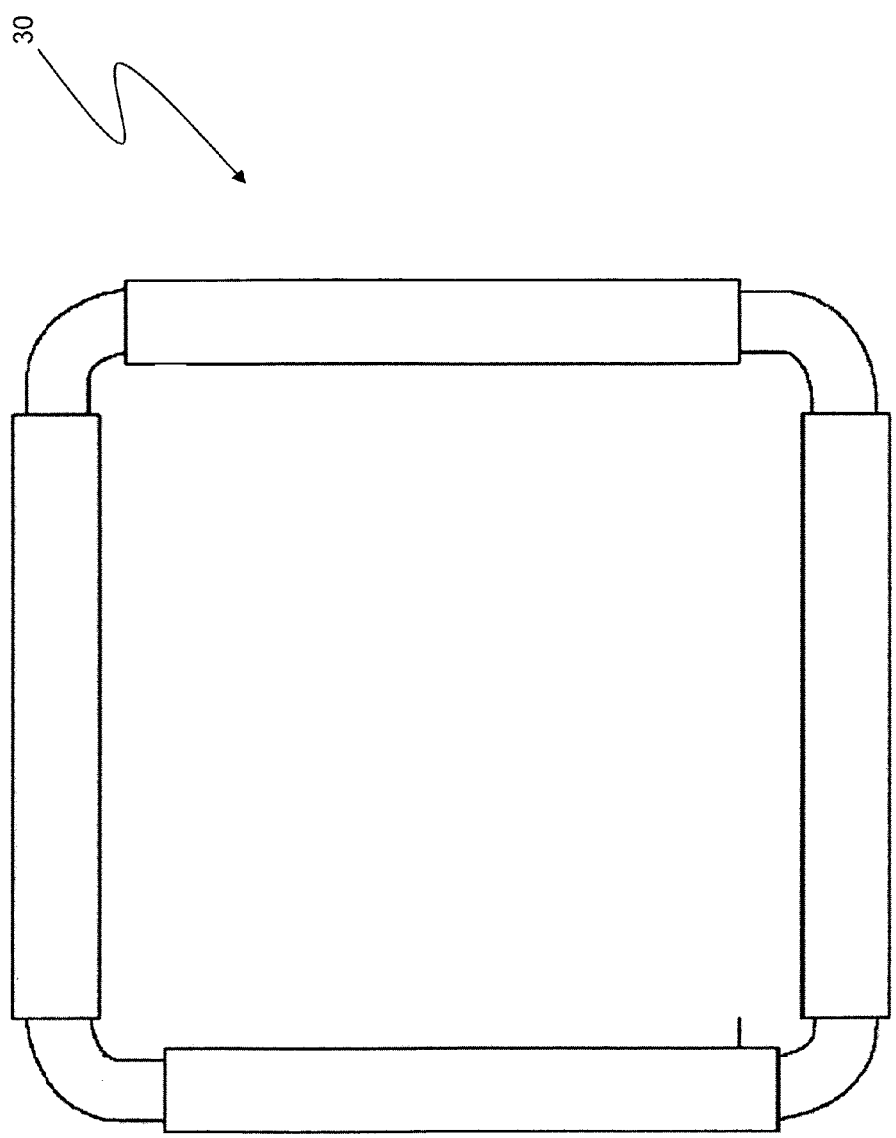
FIG. 7 is a top view of an embodiment stiffening system.

Reference is drawn to FIGS. 1-5, which are different views of an embodiment infant mattress 10. The mattress 10 includes a core mattress 20, with an optional stiffening system 30, and a mattress cover 40. Depending upon the intrinsic stiffness or rigidity of the core mattress 20, the core mattress 20 may be further reinforced with the stiffening system 30. FIG. 6 is a top view of an embodiment stiffening system 30. The stiffening system 30 may prevent the core mattress 20 from bending when under the weight of an infant 1. As shown in the figures, in preferred embodiments the stiffening system 30, if present, is disposed within the core mattress 20. The stiffening system 30 may be made from any suitable material, such as plastic, wood or metal and may provide a tube-like or frame-like structure to reinforce the core mattress 20.

The core mattress 20 may be made from a resilient material. For example, in certain embodiments the core mattress 20 is made from polyurethane foam. In other embodiments the core mattress 20 is made from a mixture of polyurethane foam and polyester, such as 93% polyurethane foam and 7% polyester. In other embodiments the core mattress 20 is made from natural latex. Other suitable materials with requisite resilience and stiffness may be employed for the core mattress 20, either alone or in combination with the stiffening system 30.

The core mattress 20 has a bottom surface 21, which may serve as a base for the mattress 10, and a top surface 23. The top surface 23 may be inclined with respect to the bottom surface 21, and hence the infant 1 may lie at an inclined angle with respect to the base surface 21 so as to help prevent gastro-esophageal reflux. That is, the height of the core mattress 20 may increase from an anterior end 12 to a posterior end 14. The angle of inclination may be, for example, from 20 to 30 degrees. The infant 1 is aligned on the mattress 10 so that the feet are towards the anterior end 12 while the head points towards the higher posterior end 14. By way of a specific example, the core mattress 20 may have a width from left side 16 to right side 18 of about 27 to 28 inches, and a length from anterior end 12 to posterior end 14 of about 36 inches. The anterior end 12 of the core mattress 20 may have a height of about 2 to 3 inches, while the posterior end 14 may have a height of 12 inches.

It is preferred that at least the top surface 23 of core mattress 20 be moisture resistant, and preferably the entire core mattress 20 is moisture resistant. Any suitable means may be employed to make the core mattress 20 resistant or impermeable to moisture. For example, the external surfaces 21, 23 of the core mattress 20 can be enveloped in, or coated with, an impermeable plastic sheet, such as a vinyl laminate cover. Additionally, preferred embodiment core mattresses 20 are fire retardant.

The top surface 23 of core mattress 20 includes a depression 22 for accepting the head and torso of infant 1. For purposes of the following, it should be understood that the term "depression" is intended to include both indentations in the top surface 23, holes in the core mattress 20, and combinations thereof. By way of example, the depression 22 may have a width of about 14 inches, and a length of about 17 inches; the posterior end 14 of depression 22 may be spaced about 4 inches from the posterior end 14 of core mattress 20.

The anterior end 12 of depression 22 may include a surface 24 that acts as a buttock stop for the infant 1. Because the infant 1 may rest in an inclined position, the infant 1 may have a tendency to slide towards anterior end 12. However, the infant 1 may further rest partially disposed within depression 22. Hence, buttock stop 24 serves to support the buttocks of the infant 1 to prevent any anterior sliding of infant 1. Buttock stop 24 may have an angle of 20 to 30 degrees, for example, with respect to bottom surface 21. The lower legs and feet of the infant 1 may thus rest on the anterior end 12 of the top surface 23, while the upper legs or buttocks of the infant 1 rest against the buttock stop 24 and the remainder of the infant 1 rests above the bottom surface 25 of depression 22, as discussed in more detail below.

Figure 8:
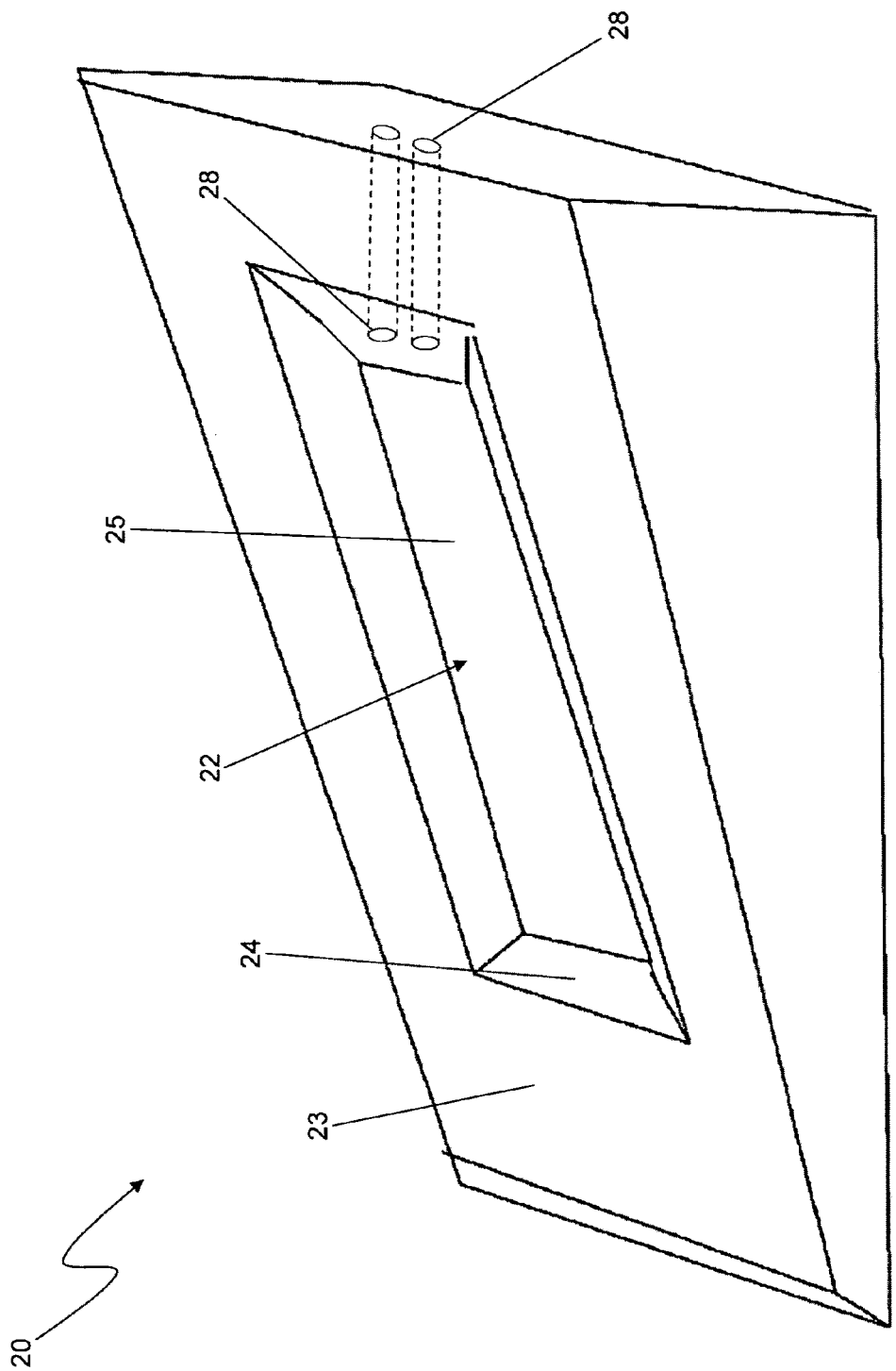
FIG. 8 is a perspective view of another embodiment core mattress without the mattress sheet.

In certain embodiments the depression 22 further includes another, second depression 26. This second depression 26 acts as a catchment or reservoir to collect any secretions, such as regurgitations, of the infant 1. Disposed within the catchment 26 may be a removable tray 50, made, for example, of plastic. An absorbent material 52 or like may further line the tray 50. Alternatively, only the absorbent material 52 may be used to collect moisture within catchment 26. In yet other embodiments, as shown in FIG. 8, no distinct catchment 26 need be present, and an absorbent material 52, tray 50 or both may be used to line bottom surface 25 of depression 22.

For various embodiments, the posterior end 14 of depression 22 may further include one or more openings 28 in the core mattress 20. It will be appreciated, of course, that the openings 28 may be placed anywhere within the sidewalls of the depression 22, however. The openings 28, in communications with external (i.e., external to depression 22) air or air sources, may facilitate the circulation of air within the depression 22. Additionally, posterior or external end 14 of the one or more openings 28 may be adapted to receive a supply tube 60 to provide oxygen or aerosols to the infant 1 via the depression 22. Hence, one or more of the openings 28 may be internally reinforced with a suitable tubing. In some embodiments, one or more of the openings 28 are slits in the core mattress 20. As known, oxygen and aerosols may be distributed by wall tubes in a hospital, or by bottles or devices; one or more of the openings 28 may therefore have a connector adapted to mate with such supply sources. In this manner various embodiment mattresses 10 may accommodate respiratory diseases of the infant 1, if present.

Mattress cover 40 covers the top surface 23 of the core mattress 20, and preferably envelopes the entire core mattress 20. For embodiments in which the cover 40 does not envelope the core 20, an anchoring system at the anterior 12, posterior 14, left 16 and right 18 ends may be used to secure the cover 40 to the core 20 or to a crib. Any suitable anchoring system may be employed, such as snaps, hooks, VELCRO® (hook and loop fastener) or the like.

In the preferred embodiments the mattress cover 40 has a bag-like shape that can be closed with a closing mechanism 48, such as a zipper, buttons, VELCRO® (hook and loop fastener) or the like. The shape of the mattress cover 40 may be tailored to the specific shape of the core mattress 20 to provide a snug fit of the cover 40 over the core 20. The cover 40 may thus be removed from the core 20, such as for cleaning. The core 20 may subsequently be inserted into the cover 40 and the closing mechanism 48 closed to secure the cover 40 over the core 20.

In preferred embodiments the mattress cover 40 is formed from two distinct types of fabric for corresponding regions of the core mattress 20. The cover 40 includes a mesh-like fabric 44 that is disposed across the depression 22 of the core mattress 20. The mesh-like fabric 44 serves as a hammock upon which the head and torso of the infant 1 lie, and may be made, for example, from cotton. For those portions of the fabric 44 that are in contact with the infant 1, the width of the webbing that makes up the mesh-like structure 44 is ideally less than the width of the fingers of infant 1, such as less than ⅛ of an inch. In certain embodiments, the mesh-like fabric 44 may further include an underlying reinforcing mesh, such as made from nylon. Hence, the mesh-like hammock 44 may be formed from two separate materials: a soft, upper material upon which the infant 1 lies in direct contact, which has a relatively narrow webbing spacing (i.e., less than the width of the fingers of infant 1), and an optional underlying reinforcing mesh that the infant 1 does not directly contact that provides additional support for the hammock 44. The remainder 42 of the cover 40 may be made from another type of fabric, such as a standard cotton cloth or the like, and corresponds to those regions of the core mattress 20 that are external to the depression 22. In certain embodiments, the reinforcing material for the hammock 44, if present, may be attached (for example, by way of a zipper, snaps, VELCRO® (hook and loop fastener) or the like) around the depression 22 to reinforce the hammock 44 provided by the topmost mesh fabric. In yet other embodiments, the remainder 42 of cover 40 may also be further provided with an additional mesh-like fabric to provide reinforcement against the weight of infant 1.

The mesh-like portion 44 of the cover 40 permits fluids from the infant 1 to easily fall onto bottom surface 25 of depression 20, such as into the catchment 50, without pooling on the cover 40. The mesh-like surface 44 also ensures that a maximum amount of airflow is available to the infant 1, which is particularly important if the infant 1 has turned onto his or her stomach. The curvature of the hammock 44 may also help to prevent plagiocephaly. Air flow from openings 28 helps to avoid the re-breathing of air. The openings 28 may also permit the administration of therapeutic amounts of oxygen or aerosols. The mesh-like portion 44, including any underlying supportive layer if present, is preferably tailored to conform with buttock stop 24 so that when the infant 1 lies in the hammock provided by mesh-like portion 44, the buttocks of the infant 1 rest comfortably against the stopping surface 24. The hammock 44 is preferably less deformable than the core mattress 20, and hence underlying supportive webbing may be desirable to reinforce the softer, upper webbing of the hammock 44 that contacts the infant 1. As indicated, the core mattress 20 may deform under the weight of infant 1. The depth of the hammock 44 (i.e., how far hammock 44 extends into depression 22) may thus be a function of the width of mesh-like fabric 44, resiliency of mesh-like fabric 44 (in combination with any underlying reinforcing mesh), the width of depression 22, and the resiliency of core mattress 20. Hence, in embodiments where the core mattress 20 readily deforms under the weight of infant 1, it may be desirable to have the hammock portion 44 disposed relatively tightly over the depression 22 so that the final desired curvature of the hammock 44 is achieved under the weight of the infant 1. For example, the hammock 44 may initially be flat, but subsequently curve under the weight of the infant 1.

The mattress cover 40, and any water-proofing material over the core mattress 20, may further include one or more holes 46 that are aligned with the one or more openings 28 so that air may freely circulate through the openings 28, and so that an external supply 60 may access the openings 28. In place of holes 46, the mattress cover 40 may employ a mesh-like material that permits the free, unobstructed circulation of air. In other embodiments, the top surface 23 of core mattress 20 within depression 22 may have a secretion trail for the removal of fluids; in such embodiments, a suitable slit or opening may be made in any of the sidewalls of depression 22 in the core mattress 20 to effect removal of such secretions.

Figure 9:
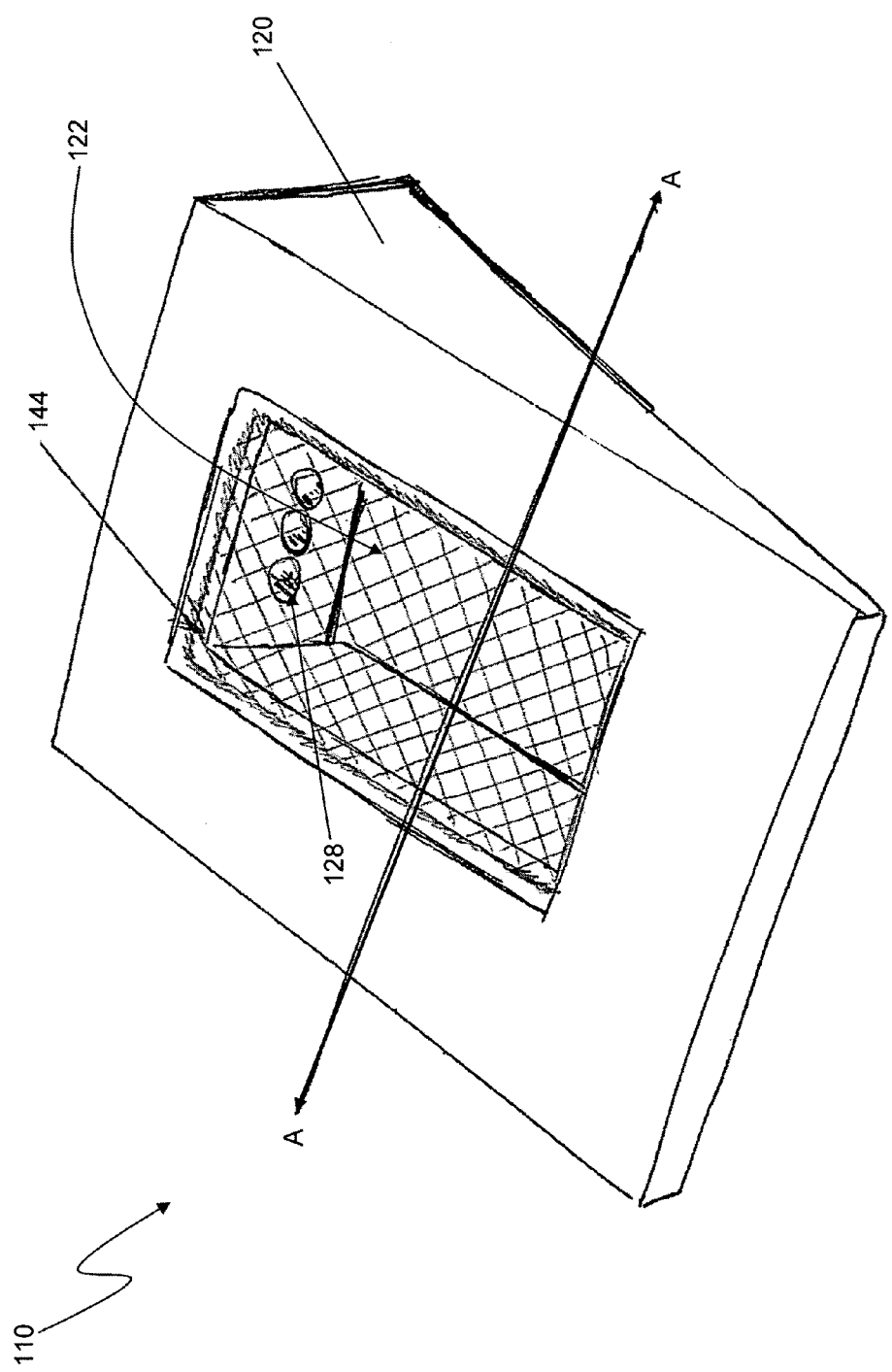
FIG. 9 is a perspective view of yet another embodiment infant mattress.
Figure 10:
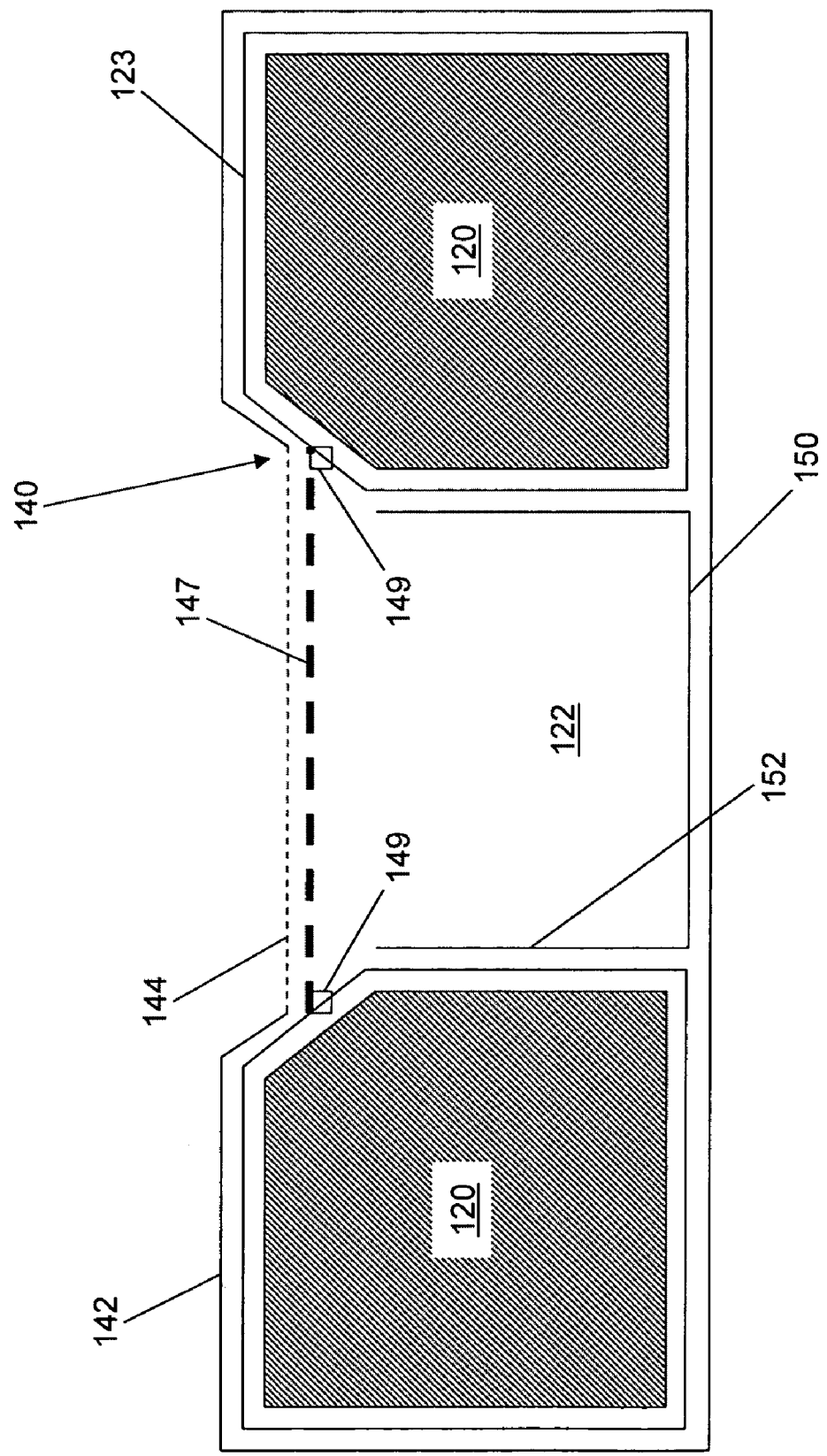
FIG. 10 is a cross-sectional view of the infant mattress shown in FIG. 9 along line A-A.

FIG. 9 provides a perspective view of another embodiment infant mattress 110. FIG. 10 is a cross-sectional view of the infant mattress 110 along line A-A. Infant mattress 110 includes a core mattress 120 that has a hole through the entirety of its height to form the depression 122. One or more sidewalls of the depression 122 may include one or more openings 128 to provide for circulation of air or the dispensing of oxygen or aerosols within the depression 122. The core mattress 120 may include a water-proofing layer 123, which is preferably an impermeable sheet material such as a vinyl sheet or the like. Cover 140 may be removably disposed over the core mattress 120 and includes a soft, mesh-like fabric 144 to provide a hammock over the depression 122. The cover 140 may also include another underlying mesh-like fabric 147 disposed under the upper mesh-like fabric 144 to provide additional support for the hammock when under the weight of an infant. The underlying reinforcing mesh 147 may, for example, be removably attached to the core mattress 120, or to the water-proofing cover 123, by any suitable attaching mechanism 149, such as zippers, VELCRO® (hook and loop fastener) or the like. Alternatively, the underlying mesh 147 may be attached to the cover 140. In certain embodiments the underlying mesh 147 also extends under the remainder portions 142 of cover 140 that are external to the depression 122 to provide reinforcement over the entirety of cover 140.

A tray 150 may be disposed within the depression 122. The tray 150 is preferably removable from the depression 122. Depending upon the height of openings 128 and the height of the sidewalls 152 of tray 150, the tray 150 may also include openings (not shown) in register with the openings 128. The tray 150 serves to catch any fluids from the infant disposed on the hammock portion 144 and also serves as a stiffening system for the core mattress 120. Hence, the tray 150 may provide the bottom surface of depression 122, serving to both close the hole formed by depression 122 and also to provide mechanical support to the core mattress 120. Note that in embodiments in which the tray 150 is not present, the bottom surface of depression 122 would be provided by the surface upon which the infant mattress 110 rests.

The hammock provided by mesh-like fabric 144 and underlying mesh 147, in conjunction with depression 122, ensures that the infant is provided a maximal amount of clean, fresh air, which is believed to assist in preventing SIDS. The conformal curvature of the hammock with the infant's skull may also help to avoid plagiocephaly. Additionally, the impermeable sheet 123 may also help to prevent SIDS in accordance with the so-called GAZ theory of SIDS. The GAZ theory of SIDS postulates that infant crib death may be caused by highly toxic nerve gases that may be generated from mattresses used in the cribs of babies. The gases are presumed to be generated by the action of common household fungi on compounds of phosphorus, arsenic and antimony that are often present in infant mattresses, particularly mattresses that are damp with sweat, milk or contaminated with urine. Consequently, it is believed that preventing exposure of the infant to such toxic gases will prevent SIDS. Various embodiments avoid exposure to such gasses, if present, by wrapping the core mattress 120 with a gas impermeable sheet 123. The infant thus lies on a hammock surrounded by clean, fresh air. Even for embodiments that do not have the impermeable sheet 123, the mattress ventilation allows air flow, which may lower sweating of the infant. Moreover, liquids, such as milk, urine, vomit or the like, fall into the plastic reservoir 150 and so will not contaminate the core mattress 120.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. An infant mattress comprising: a core mattress made from a resilient material comprising a bottom surface and a top surface which is inclined with respect to the bottom surface, the top surface comprising a first depression sized to at least partially accept the torso and head of an infant; and a fabric, bag-shaped mattress cover removably disposed around the core mattress and comprising a first fabric forming a first mesh disposed across at least a portion of the depression, the first mesh forming a hammock suspended over a bottom surface of the depression and onto which the head, torso or both of the infant may be disposed and thereby suspended over the depression or hole.

2. The infant mattress of claim 1 wherein the mattress cover further comprises a closing mechanism to close an opening of the bag-shaped structure.

3. The infant mattress of claim 1 wherein at least one sidewall of the first depression comprises an opening for providing air or aerosols to the depression, and the mattress cover comprises a hole aligned with the opening.

4. The infant mattress of claim 3 wherein an external end of the opening is adapted to connect to a supply tube.

5. The infant mattress of claim 1 wherein an anterior end of the first depression comprises a stopping surface adapted to abut against the buttocks or upper legs of the infant to prevent the infant from sliding towards the anterior end of the infant mattress.

6. The infant mattress of claim 1 further comprising a stiffening system to impart rigidity to the core mattress to substantially reduce bending of the core mattress under the weight of the infant.

7. The infant mattress of claim 6 wherein the stiffening system is disposed within the core mattress.

8. The infant mattress of claim 6 wherein the stiffening system is a tray disposed within the depression.

9. The infant mattress of claim 1 wherein a bottom surface of the first depression further comprises a tray, absorbent material, or both for collecting fluids from the infant.

10. The infant mattress of claim 9 wherein the tray, absorbent material or both are disposed within a second depression within the first depression.

11. The infant mattress of claim 1 further comprising a second fabric forming a second mesh disposed under the first mesh to provide additional support for the hammock.

12. The infant mattress of claim 11 wherein the second mesh is removably connected to the core mattress or to a water-proofing layer disposed over the core mattress.

13. The infant mattress of claim 1 wherein an external surface of the core mattress further comprises a water-proofing layer.

14. The infant mattress of claim 13 wherein the water-proofing layer is gas impermeable.

15. The infant mattress of claim 1 wherein the core mattress has a hole through the entirety of its height to form the depression.

* * * * *